(12) United States Patent
Wang et al.

(10) Patent No.: US 7,712,955 B2
(45) Date of Patent: May 11, 2010

(54) NON-CONTACT METHOD AND APPARATUS FOR HARDNESS CASE DEPTH MONITORING

(76) Inventors: Chinhua Wang, Apt. 301, Building #8, Hua Qiao Hua Yuan, 188 Ren Min Road, Suzhou, Jiangsu Province (CN) 215006; Jose A. Garcia, 14 Blakley ave., Toronto, Ontario (CA) M6N 3Y5

( * ) Notice: Subject to any disclaimer, the term of this patent is extended or adjusted under 35 U.S.C. 154(b) by 99 days.

(21) Appl. No.: 12/002,259

(22) Filed: Dec. 17, 2007

(65) Prior Publication Data

US 2009/0154521 A1 Jun. 18, 2009

(51) Int. Cl.
G01N 25/00 (2006.01)
G01N 17/00 (2006.01)
G01J 5/00 (2006.01)

(52) U.S. Cl. .......................... 374/7; 374/121; 374/131; 374/57

(58) Field of Classification Search .................. 374/7, 374/121, 131, 57
See application file for complete search history.

(56) References Cited

U.S. PATENT DOCUMENTS

| 4,551,030 | A | * | 11/1985 | Luukkala et al. ............... 374/5 |
| 4,710,030 | A | * | 12/1987 | Tauc et al. ................. 356/432 |
| 5,118,945 | A | * | 6/1992 | Winschuh et al. ......... 250/341.4 |
| 5,486,924 | A | * | 1/1996 | Lacey ......................... 356/507 |
| 5,604,592 | A | * | 2/1997 | Kotidis et al. ............... 356/493 |
| 5,667,300 | A | * | 9/1997 | Mandelis et al. .............. 374/43 |
| 5,706,094 | A | * | 1/1998 | Maris ........................ 356/432 |
| 5,864,393 | A | * | 1/1999 | Maris .......................... 356/28 |
| 6,122,042 | A | * | 9/2000 | Wunderman et al. .......... 356/73 |
| 6,156,030 | A | * | 12/2000 | Neev ........................... 606/10 |
| 6,497,772 | B1 | * | 12/2002 | Meckel et al. ............... 148/254 |
| 6,882,424 | B2 | * | 4/2005 | Opsal et al. ................. 356/432 |
| 2006/0067379 | A1 | * | 3/2006 | Djeu .......................... 374/161 |
| 2006/0114965 | A1 | * | 6/2006 | Murphy et al. .............. 374/120 |
| 2008/0283755 | A1 | * | 11/2008 | Dazzi et al. ............ 250/339.07 |

* cited by examiner

*Primary Examiner*—Gail Verbitsky
*Assistant Examiner*—Mirellys Jagan
(74) *Attorney, Agent, or Firm*—Lynn C. Schumacher; Hill & Schumacher

(57) ABSTRACT

There is provided a method and apparatus to monitor hardness using laser infrared photothermal radiometry. The emphasis is on the ability of this invention to monitor in a non-contact and non-destructive manner the hardness case depth of industrially heat treated steels. The present invention provides a method and apparatus comprising signal generation and analysis as well as instrumental hardware configurations based on the physical principle of photothermal radiometry. The method comprises (a) irradiating the sample surface with an excitation source of suitable emission wavelength and intensity. (b) producing periodic frequency pulses of the laser beam by means of a modulator in the appropriate frequency range (but not confined to) 0.1-100000 Hz. (c) passing the emitted beam through appropriate optics for beam conditioning (d) splitting the incident beam in two beams using a beam-splitter (e) focusing one of the beams onto a photodiode connected to a lock-in amplifier referenced to the modulator frequency to monitor laser power fluctuations (f) directing the second beam normal or at an angle to the surface of the sample (g) directing the generated infrared emissions from the sample surface to an infrared detector connected to another lock-in amplifier also referenced to the modulator frequency (h) recording the signals obtained from both lock-in amplifiers by a computer (i) processing the obtained signals through proprietary software and pre-calibration curves.

22 Claims, 5 Drawing Sheets

NON-CONTACT METHOD AND APPARATUS FOR HARDNESS CASE DEPTH MONITORING

FIELD OF INVENTION

The present invention relates to a non-contact, non-destructive method and apparatus to monitor hardness case depth of industrially heat treated steels using laser infrared photothermal radiometry.

BACKGROUND OF THE INVENTION

Hardness and case depth measurements are the most important parameters for the quality monitoring of case-hardened steel products and the heat treating process. The current industrial standard technique for these measurements is micro-indentation, which is destructive and time consuming, and therefore not suitable for the need of industrial on-line volume inspection. There have been continuous efforts to search for new methods for evaluating hardness and case depth in a non-contact and non-destructive fashion. In recent years, photothermal techniques have shown strong potential for non-contact and remote hardness and case depth evaluation. A number of photothermal applications to hardness measurements in metals have been reported in the literature. Various independent research groups have reported a well-established anticorrelation between thermal diffusivity/thermal conductivity and microhardness. Jaarinen and Luukkala [see Jaarinen J, Luukkala M., J Phys (Paris) 1983; 44: C6-503] made the first attempt to study the properties of surface hardness of steel in terms of an inverse process and developed a numerical technique based on the solution of the thermal-wave equation using a two-dimensional finite difference grid. Lan et al. [see Lan T T N, Walther H G, Goch G, Schmitz B., J App Phys 1995; 78:4108-4111.] and Mandelis et al. [see Munidasa M, Funak F, and Mandelis A. J App Phys 1998; 83:3495-3498., and Ma T. C., Munidasa M., and Mandelis A., J App Phys 1992; 71, 6029-6035.], showed the capability of photoacoustic (PA) and photothermal radiometric (PTR) detection as depth profilometric techniques for case hardened steels using inverse-problem reconstruction algorithms. Both groups demonstrated anti-correlation between the case depth dependent microhardness and thermal conductivity/diffusivity of the material. Further photothermal radiometric (PTR) studies of hardness case depth profiling were carried out by Walther et al. [see Walther H G, Fournier D, Krapez J C, Luukkala M, Schmitz B, Sibilia C, Stamm H, Thoen J., Anal Sci 2001; 17:s165-168.], Fournier et al. [see Fournier D, Roger J P, Bellouati A, Boue C, Stamm H, Lakestani F. Anal Sci 2001; 17:s158-160.] and Nicolaides et al. [see Nicolaides L, Mandelis A, Beingessner., J App Phys 2001; 89:7879-7884., and Nicolaides L, Mandelis A. J App Phys 2001; 90:1255-1265]. The last group also investigated the microstructure change and the physical mechanisms of the thermal diffusivity depth-profile generation for carburized and quenched AISI-8620 steels. They showed that the variation of thermal diffusivity with depth is dominated by the carbon concentration profile, while the absolute thermal diffusivity values are dominated by microstructural changes occurring during quenching. All those investigations have focused on samples heat treated in the presence of carbon or nitrogen ambient, to form a concentration gradient which subsequently defines the hardness case depth profile after quenching. Recently, the PTR technique was also used in the characterization of non-diffusion controlled steel case depth: The hardness penetration depth of grind-hardened SAE 4140 steel using the calibration curve of case depth versus phase sum [see Prekel H, Ament Ch, Goch G., Rev Sci Inst 2003; 74:670-672.] and the effect of cooling rate on hardness and thermal diffusivity by means of water end-quenched heat treatment in a metallurgical Jominy bar made of AISI 1018 steel [see Liu Y, Baddour N, Mandelis A, Wang C H., J App Phys 2004; 96:1929-1933], were evaluated. As is well known, the PTR signal is sensitive to both thermophysical properties and sample geometry. To simplify geometry effects, all reports to-date concern laboratory based investigations, in which all samples were well defined, prepared and machined flat surfaces with a good finish. Recently, the evaluation of machined cylindrical samples was reported in order to demonstrate the feasibility of the PTR technique with non-flat geometries [Wang C H, Mandelis A, Liu Y., J App Phys 2004; 96:3756-3762. Wang C H, and Mandelis A, Liu Y. J App Phys 2005; 97:014911]. In those studies it was shown that thermal-wave interference occurs in layered curved samples and the details of the interferometric pattern are affected by the degree of curvature.

The present invention is concerned with the capabilities of the photo-thermal radiometric method (PTR) in measuring the effective case depth in case-hardened industrial steels in a non-contact and non-destructive manner. The method and some possible embodiments of the apparatus are presented below.

SUMMARY OF THE INVENTION

The present invention provides a non-contact and non-destructive method and apparatus for measurement of the effective case depth of heat treated parts based on laser photothermal radiometry.

Accordingly, in one aspect of the present invention, there is provided a method of determining a case depth of a hardened sample comprising a material, the method comprising the steps of:

a) providing a modulated reference signal;

b) modulating an intensity of an optical beam according to the modulated reference signal using a modulation means;

c) measuring an unhardened reference sample comprising the material by scanning a frequency of the modulated reference signal over selected frequencies within a frequency interval, while performing the following steps at each selected frequency;

i) irradiating a surface of the reference sample with the optical beam, ii) collecting thermal radiation emitted by the reference sample and directing the collected thermal radiation onto a broadband detector;

iii) determining a reference sample phase difference between a signal obtained from the broadband detector and the modulated reference signal;

d) measuring the hardened sample by scanning a frequency of the modulated reference signal over the selected frequencies within the frequency interval, while performing the following steps at each the selected frequency;

v) irradiating a surface of the hardened sample with the optical beam, vi) collecting thermal radiation emitted by the hardened sample and directing the collected thermal radiation onto a broadband detector;

vii) determining a hardened sample phase difference between a signal obtained from the broadband detector and the modulated reference signal;

e) calculating a normalized phase difference for each frequency by subtracting the reference sample phase difference from the hardened sample phase difference;

f) determining a phase-minimum frequency corresponding to a frequency at which the normalized phase difference is minimized; and g) relating the phase-minimum frequency to the case depth using a pre-determined calibration curve.

In another aspect of the present invention, there is provided an apparatus for use in determining a case depth of a hardened sample, the apparatus comprising:

a) means for providing a modulated reference signal;

b) an optical source providing an optical beam;

c) modulation means for modulating an intensity of the optical beam according to the modulated reference signal;

d) a broadband detector adapted to detect thermal radiation;

e) an optical fiber bundle having first, second and third ends, the optical fiber bundle comprising a beam delivery optical fiber and one or more collection optical fibers; wherein the beam delivery optical fiber comprises:

an input adapted to receive the optical beam at the first end; and an output adapted to direct the optical beam onto the sample at the second end; and wherein the one or more collection optical fibers each comprise:

an input adapted to collect thermal radiation emitted from the sample at the second end; and an output adapted to direct the collected thermal radiation onto the detector at the third end; and f) processing and output means for determining a phase difference between a phase of a signal obtained from the detector and a phase of the modulated reference signal and one of displaying the phase difference, recording the phase difference, and the combination thereof.

BRIEF DESCRIPTION OF THE DRAWINGS

The apparatus for monitoring hardness and effective case depth according to the present invention will now be described by way of example only, reference being had to the accompanying drawings in which.

DETAILED DESCRIPTION OF THE INVENTION

The current invention is based on laser photothermal radiometry, a non-intrusive non-contacting technique, to monitor effective case depth of industrially heat treated parts.

Apparatus

Figure 1:
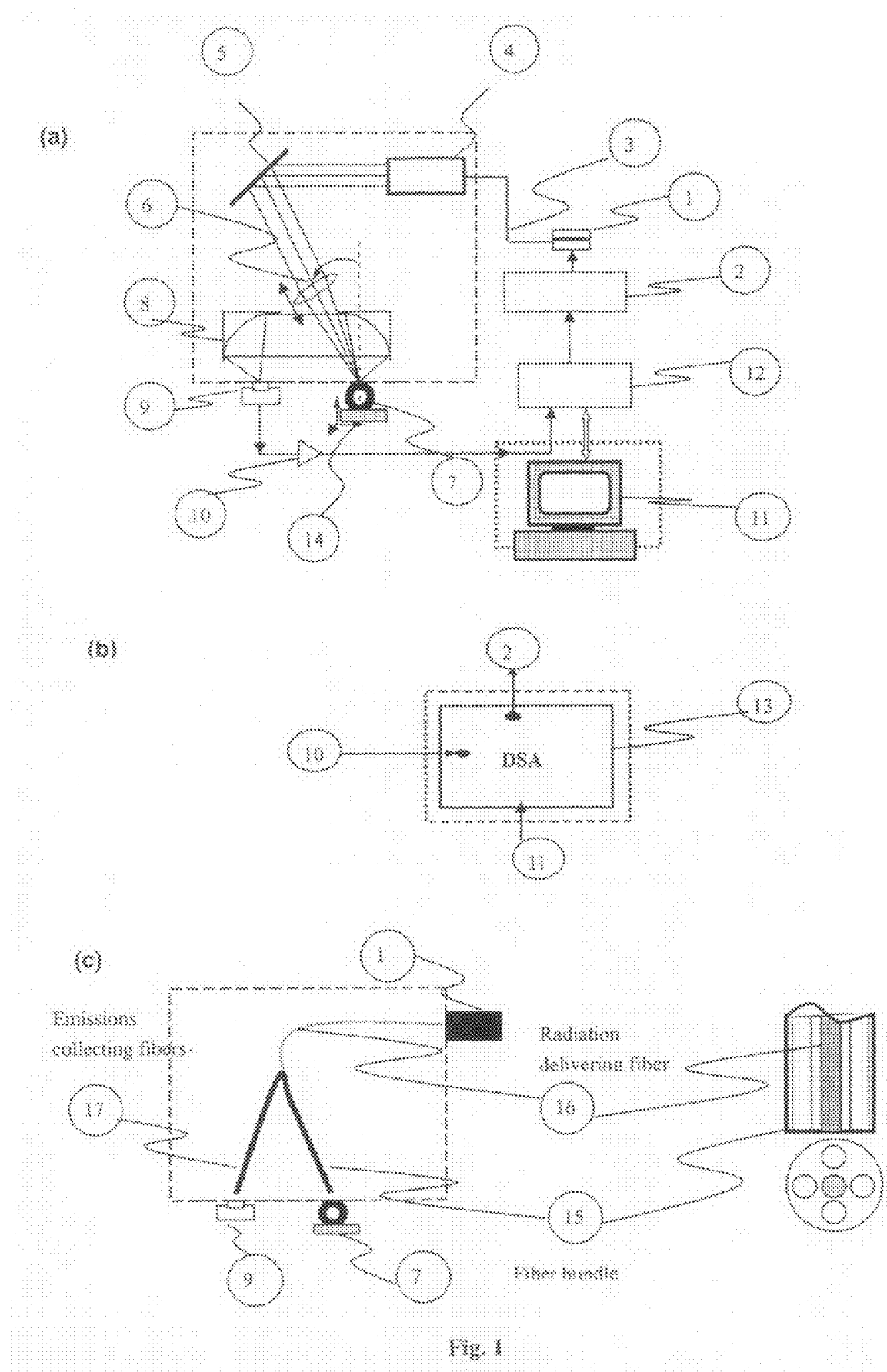
FIG. 1 illustrates a schematic diagram of possible embodiments of the hardness monitoring apparatus with a) Lock-in point-by-point frequency-scan configuration. (b) Swept-sine wide-bandwidth configuration using a dynamic signal analyzer and (c) optical path using fiber optics bundle. The optical path in FIG. 1a is the same as that in FIG. 2a, but the block surrounded by dotted lines in FIG. 2a is replaced by FIG. 2b. For the third embodiment the optical path in FIG. 1a surrounded by the dashed line and is replaced by FIG. 1c.

A schematic diagram of possible embodiments of an instrument for hardness case depth monitoring is shown in FIGS. 1a, 1b, and 1c. The excitation source is a high power semiconductor laser 1 capable of heating the material under examination. The laser power output was modulated by using a current driver 2 controlled by a personal computer 11 resulting in a harmonic energy source or beam 3 that is directed using an expander 4 a mirror 5 and lens 6 onto the sample 7. The beam was focused or expanded depending on the measurement scheme, and then impinged onto the surface of the sample with a spot size between 1 and 22 mm by adjusting the position of the converging lens 6. A pair of off-axis paraboloidal mirrors, 8 are aligned with the focal point coincident with that of the laser beam and used to collect emitted IR photons from the sample. The collected IR emissions are focused onto a detector 9 after being passed through a filter that allows Planck-mediated thermal infrared emission band in the spectral range (2-to-12 .mu.m). The signal is then preamplified with pre-amplifier 10 and demodulated using a lock-in amplifier 12. The entire data acquisition process is controlled using a personal computer 11. Another instrument configuration includes using a 2-channel signal analyzer 13 instead of the lock-in amplifier 12. The optical path is the same as in FIG. 1a; the block surrounded by the dotted line in FIG. 1a is replaced by the block surrounded by the dotted line in FIG. 1b. This measurement scheme employs a 2-channel dynamic signal analyzer, FIG. 2b, to fast generate a sine-wave signal with linearly swept frequency f=f(t) which serves as a reference waveform as well as input to the current driver 2 of the diode laser 1. The analyzer cross-correlates the reference sine-wave signal and the PTR output signal from the detector 9 and through spectral analysis it generates and outputs the amplitude and phase vs. frequency of the PTR signal in real time. A third embodiment replaces the optical path components shown in the box with dashed line by one with a fiber optic bundle 15 shown in the dashed line box of FIG. 1c. In this arrangement all other components remain the same but the laser beam is delivered to the sample via a central optical fiber 16 of the fiber optic bundle. The infrared emissions from the sample are then collected by concentric optical fibers 17, located around the central optical fiber, and focused to detector 9.

Method

1. Experimental Tests

The samples tested were made of C1018 steel (composition: 0.14%-0.2% C, 0.6%-0.9% Mn). Three types of screws with different screw heads (i.e., hexagonal with 6 flat surfaces, cylindrical and spherical heads) were evaluated. Two measurements were made on the heads of screws, on spots 1 and 2 for each screw. There were 10 samples of each type of screw and each hardened case depth. Four nominal hardness case depths (0.01, 0.02, 0.03 and 0.04 inch) were delivered by the heat treating plant for each type of screw. The actual case depth was measured by a conventional indenter and was correlated to results from the PTR technique. All the samples underwent standard industrial carburizing heat treatments to obtain different case depths. For the same nominal case depth all three types of screws were grouped together to have exactly the same heat treatment. After hardening, all the screws were tested using PTR frequency scans, and then subgroups of each type of case hardened screw were subjected to mechanical indentation measurements while the remaining screws were not indented and served as a reference group. The case depths of these latter screws were estimated using the calibration curves generated from the indented groups.

The experimental setup used for these experiments is shown in FIG. 1a. The optical source was a high-power semiconductor laser (Jenoptik, max. ~20 W). The output of the laser was modulated by a periodic current driver (high-power laser diode driver, Thor Labs), the frequency of which was controlled by the computer and also served as the lock-in reference. The beam was focused or expanded depending on the measurement scheme, and then impinged onto the surface of the sample with a spot size between 1 and 22 mm by adjusting the position of the converging lens. The measurement spot (spot 1 or spot 2) on the sample coincided with the focal point of one of the off-axis paraboloidal mirrors. The harmonically modulated infrared radiation from the sample surface was collected by the off-axis paraboloidal mirrors and detected by a HgCdTe detector (EG&G Judson Model J15016). The signal from the detector was amplified by a low-noise preamplifier (EG&G Judson PA101) and then fed into a lock-in amplifier (EG&G Instruments Model 7265) interfaced with a PC. The frequency scan from 2 Hz to 10 kHz generated thermal waves the diffusion length of which covered most of the case depths of industrial relevance. A total of 50 frequency data points were recorded for each scan. FIG. 1b shows an alternate measurement modality using sine-swept excitation waveforms and cross-correlation signal analysis. While the experimental set-up and the optical path are the same as in FIG. 1a, the block surrounded by the dotted line in FIG. 1a is replaced by FIG. 1b. In the experiments, two beam profiles were employed to test the sensitivity of case depth probing to thermal-wave dimensionality, i.e., focused beam (Dia. ~1 mm) and expanded beam (Dia. ~22 mm). In order to eliminate the instrumental transfer function, a C1018 flat surface sample (Dia. ~20 mm) was used to normalize the sample signal in the form of the ratio of amplitudes and the difference of phases between sample and reference signals.

2. Experimental Results 3.1 PTR Measurements

All samples were measured using either a focused beam or an expanded beam before and after the hardening process. Considering the usual variations in geometry, surface finish or surface color in industrial volume products, each sample was measured on two spots. Then all the measurement data for the same type of screw and the same hardness case depth were statistically processed in order to generate a meaningful calibration curve (or calibration band) for industrial applications. It should be noted that only the results of normalized PTR phase are meaningful, because the amplitude of the signal is sensitive to sample surface optical conditions and reflectivity changes which may produce artifacts. Phase signals, on the other hand, are independent of surface reflectivity and lead to pure thermal-wave measurements free of such artifacts [see Liu Y, Baddour N, Mandelis A., J Appl Phys 2003; 94:5543-5548]. Normalized PTR phase measurement were obtained for cylindrical head screws before hardening using a focused and an expanded beam, respectively. The phase shape difference between focused and expanded beam, especially in the low frequency range, was attributed to the well-known dimensional effects of thermal-wave propagation [see Mandelis A., *Diffusion-Wave Fields. Mathematical Methods and Green Functions*. Springer, New York (2001)].

The mean value and standard deviation in the plots were obtained based on a group of 10 samples and a total of 40 measurements from this group. They served as baseline values and as a reference for the measurements with hardened samples.

Figure 2:
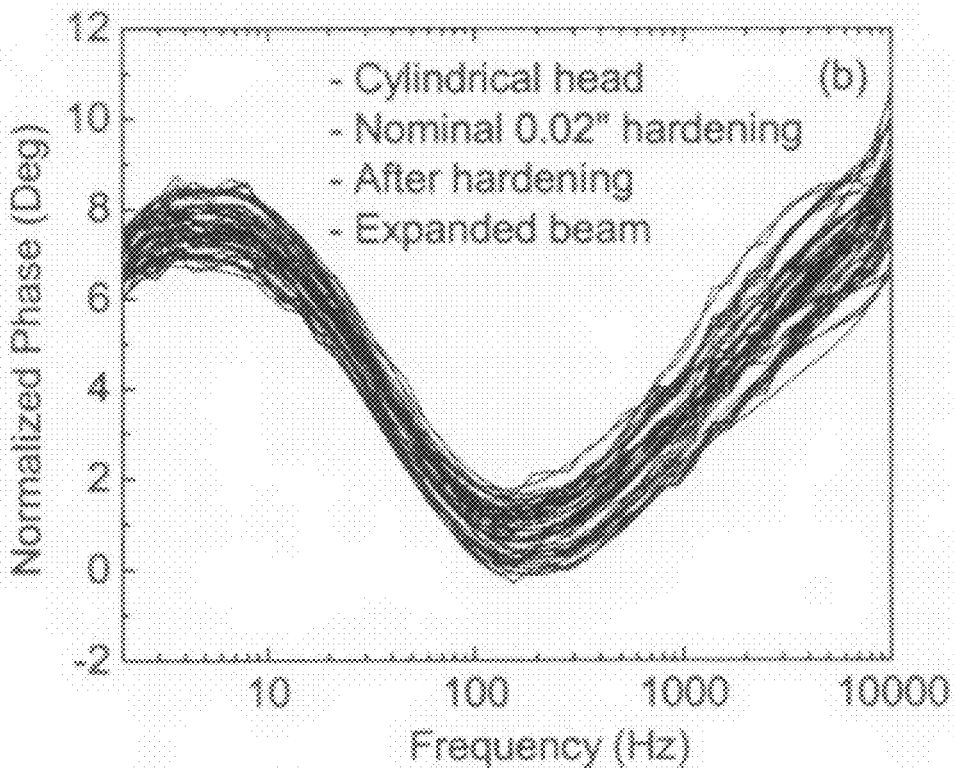
FIG. 2. Typical PTR phase frequency scans of groups of cylindrical-head screws. Nominal case depth (a) 0.01"; (b) 0.02". Laser beam size: 22 mm.
Figure 3:
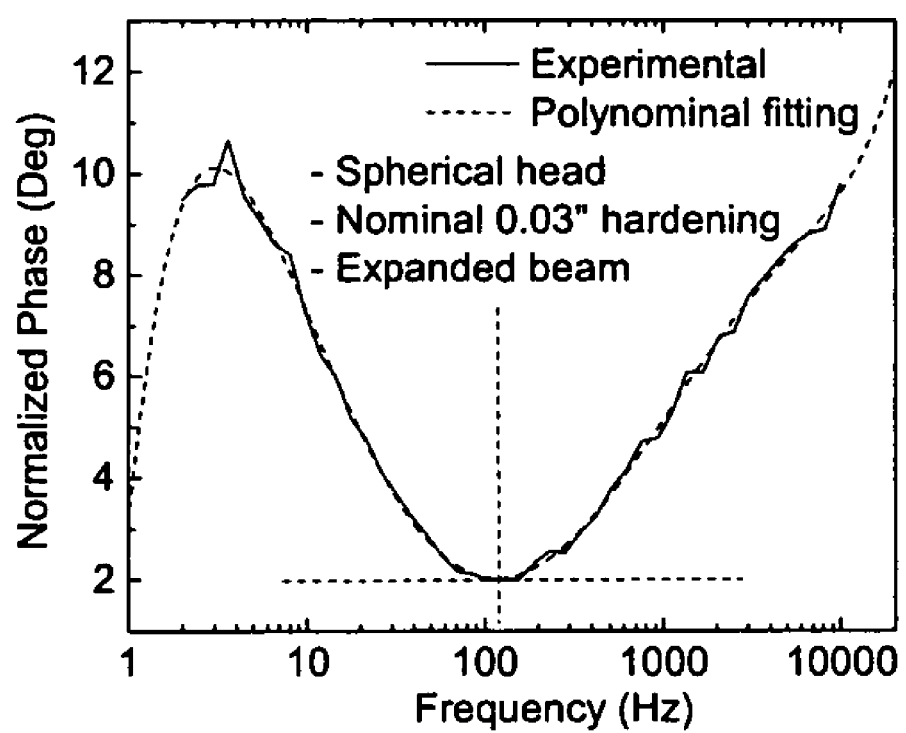
FIG. 3. Correlation between the PTR phase minima and the mechanically determined effective case depth for cylindrical-head screws using a focused beam (a) and an expanded beam (b).
Figure 4:
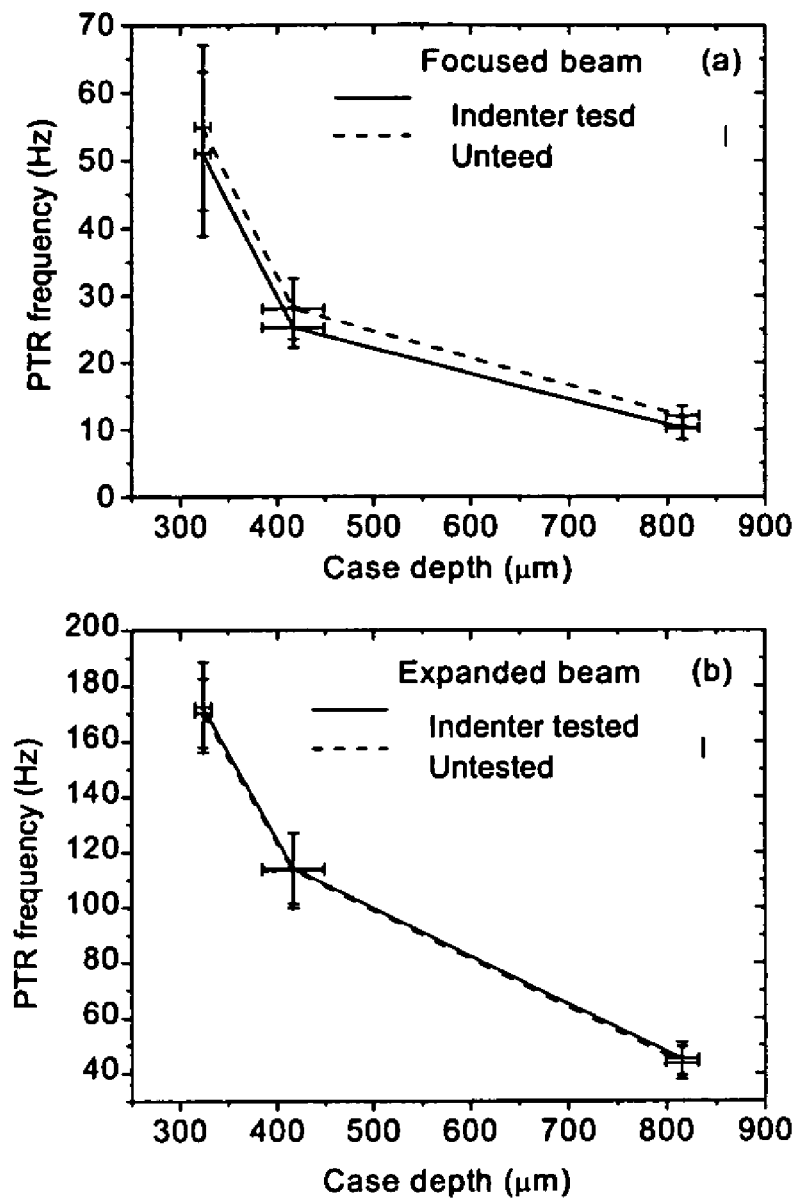
FIG. 4. Experimental data and their polynomial best fit for a spherical-head screw with a nominal 0.03" case depth hardening using an expanded beam.

FIG. 2 shows typical PTR frequency scans for the hardened (nominally 0.02" case depth) cylindrical-head screws using an expanded beam. The figure show consistency in shape and give a measure of natural variations from sample to sample. The largest variations are observed at the high frequency end, as expected [see Nicolaides L, Mandelis A., J App Phys 2001; 90:1255-1265.], due to the surface roughness and the commensurably short thermal diffusion length which probes the randomly distributed intra-roughness region, thus producing substantial variation to the overall PTR phase. In the low frequency range, both phases exhibit interferometric phase minima between ca. 10 Hz and 1000 Hz, depending on the beam size. The phase minimum was more pronounced using the expanded beam measurement than that using the focused beam. The phase minima in the plots are the result of thermal-wave confinement (a diffusive standing wave) between substrate and surface hardened layer [see Wang C H, Mandelis A, Liu Y, J App Phys 2005; 97:014911]. For a fixed overlayer thickness, in a manner analogous to freely propagating (rather than diffusing) wave fields, the height of the thermal-wave antinode depends on the difference in thermophysical properties between hardened layer and unhardened substrate. Furthermore, thicker upper layers result in antinodes of larger height, such as those shown for 0.01" nominal case depth. In these measurements the shallow antinode corresponded to 0.01" case depth, whereas the deeper antinode corresponded to 0.02". In terms of dimensionality, a wide beam mostly generates one-dimensional (forward) thermal-wave confinement within the hardened region which is more sensitive to the actual hardness boundary (or gradient), whereas a focused beam results in significant thermal-wave signal contributions from all radial directions, thus diminishing the overall importance of the forward direction and of the case boundary. In some cases of shallow case depths (~0.01"), focusing the laser beam resulted in complete elimination of the phase minimum. Therefore, 0.01" represents the minimum case depth detection limit using a focused laser beam. This is not a lower limit when a broad laser beam is used. Based on the fact that for these samples mechanical indenter results showed that the degree of surface hardness is independent of case depth, the effective thermophysical property change (thermal diffusivity and conductivity) of the hardened layer does not depend on the thickness of the hardened layer. Therefore, the location of the phase minimum on the frequency axis can be employed to estimate the effective case depth of the hardened layer without further data correction to account for surface hardness variations. The frequency positions of the phase minima were located by a computational polynomial fitting (a 7-order polynomial was employed) and a minimum-finding algorithm which was done using a MATLAB program based on the zero value of the polynomial derivatives. FIG. 3 shows an example of polynomial fit to data from a nominally 0.03"case depth hardened spherical-head screw using an expanded beam. The fitted 7th-order polynomial is $y(f)=3.11001+35.8927f-61.75457f^2+43.79467f^3-17.60857f^4+4.43277f^5-0.65003f^6+0.04146f^7$, from which the zero value of the derivative was found to be at 107.5 Hz. The resulting phase minima frequency locations vs. case depth are plotted in FIG. 4. For all hardened samples, a subset was chosen to undergo mechanical indentation tests in order to generate the calibration curve for the particular type of screw head geometry. The remaining samples were used as a reference group and were further compared with the mechanically tested group. The phase minima of the indentation tested and untested and expanded and focused beams are shown in FIGS. 4a and 4b, respectively. Typical statistical results from each plot showed that the minimum frequency spread for samples of the same group was ~10% and ~6-7% around the mean for focused beam and expanded beam, respectively. Similar results for other types of screws were obtained in the same manner and were also correlated with the mechanical hardness test results.

3.2 Mechanical Tests

Figure 5:
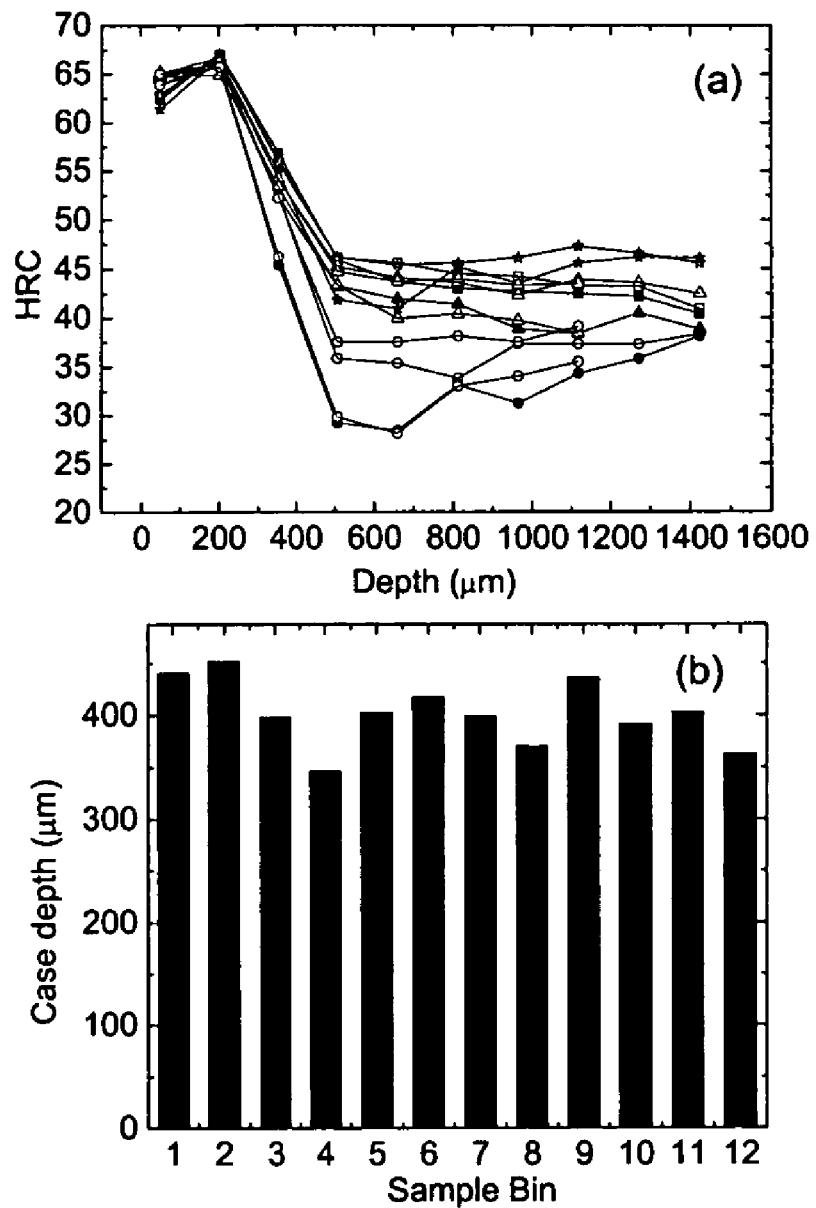
FIG. 5. Mechanical indentation hardness test results for nominally 0.03" case depth hardened hexagonal head screws

Four samples of each type of screw were chosen for hardness case depth measurements using a conventional mechanical indentation method. The samples were cut into halves, encased in resin and the microhardness was measured from both edges toward the center. Typical results are shown in FIG. 5. These results indicated that for nominally identically same hardness case depths, the variation of the hardness profile is significant, especially at large depths, although surface hardness values converge. To correct for the large baseline variations, the effective case depth, $D_{eff}$, was defined as $$D_{eff} = H_{min}^{RC} + \frac{1}{e}(H_{max}^{RC} - H_{min}^{RC}) \quad (1)$$

The effective case depths calculated from FIG. 5(a) are shown in FIG. 5(b), from which the mean case depth and standard deviation were found to be: $<D_{eff}>=401.6\pm31.9$ μm, representing a ~8-10% uncertainty (spread) for the hexagonal-head group of samples.

3.3 Correlations

Having measured the PTR phase minima and the mechanically tested hardness profiles for each type of screw, the correlation between the effective case depth and the phase minima was then established. Typical results are shown in FIG. 4. These results show these correlations in the form of calibration curves (or calibration bands, if the vertical and horizontal standard deviations are taken into account). Calibration curves were obtained for the hexagonal, cylindrical and spherical-head screws using a focused beam and an expanded beam. In the plots, mechanically tested (solid line) and untested (dotted line) results are plotted separately to view the consistency between the two groups. Operationally, the results from the destructively indenter-tested samples were used to generate the calibration curve. This curve, along with the value of each phase-frequency minimum of the remaining unindented samples of a given head type, was used to estimate the effective case depth of the unidented sample in a non-destructive manner. It was found that the two curves for all screw types and for both beam profiles shared common features. The variances of the mechanical test results are similar to those of the PTR phase minima for all case depths larger than ca. 300 μm, implying comparable sample-to-sample variations. The larger distribution in PTR measurements for some shallow case depths is attributed to increased signal variance from sample to sample which impeded accurate determination of the phase minima from the frequency scan. The reason for that is that those phase minima occur at higher frequencies since the shallower case depth confines the thermal wave closer to the sample surface within the effective overlayer [see Mandelis A. *Diffusion-Wave Fields. Mathematical Methods and Green Functions.* Springer, New York (2001)]. Phase minima located at high frequencies are affected by random surface roughness effects which tend to dominate the PTR spectrum at the high frequency end [8]. As discussed earlier on, when the case depth is very shallow, the effective thermophysical properties within the hardened layer can be greatly affected by surface roughness, yielding values controlled by a mixture of the roughness interspace gas (air), fractal heat conduction physics [Boccara A. C. and Fournier D., Optical Sciences Vol 58 (P. Hess and J. Pelzl, Eds., Springer, New York, 1988) p. 302.] and the possibly very different degree of hardness of the thin rough layer. All these complications may cause significant variation in the location of phase minima. In conclusion, the effective minimum case-depth detection limit for the C1018 steel screws using PTR phase minima was found to be ca. 300 μm. When the focused- vs. expanded-beam correlation plots are compared, the expanded beam generates larger minimum phase-frequency shifts than the focused beam for the same case depth. Furthermore, for the shallowest case depths ($\leq$300 μm) the variances of the expanded beam correlation curves were smaller than those for the focused beam curves. These facts imply that expanded beam profiles have higher resolution and dynamic range than focused beam profiles for all screw shapes and should be the preferred measurement modality.

3.4 Fast Swept-Sine Measurement

The aforementioned lock-in amplifier (LIA) based experimental scheme usually yields high signal-to-noise ratio measurements, but measurements are of relatively long duration owing to the point-by-point nature of LIA signal acquisition character and the LIA time constants (~1 s) used in the experiments, especially at low frequencies. In our experiments, 50 frequency points were measured between 0.5 Hz to 10 kHz, and 5 measurements were taken at each frequency fro averaging. Therefore, it took ~30 min. to complete one scan. To speed up measurements toward industrial on-line applications, a fast swept-sine (SS) measurement scheme was introduced. This measurement scheme employs a 2-channel dynamic signal analyzer (Stanford Research Systems Model SR785), FIG. 1b, to fast generate a sine-wave signal with linearly swept frequency f=f(t) which serves as a reference waveform as well as input to the current modulation of the diode laser. The analyzer cross-correlates the reference sine-wave signal and the PTR output signal from the detector and through spectral analysis it generates and outputs the amplitude and phase vs. frequency of the PTR signal in real time. In this measurement modality, a typical 44 points measurement between 2 Hz and 10 kHz and a 1-s time constant took ~74 s for a complete frequency sweep. Phase normalization for the LIA and the SS measurements were made, respectively, using the LIA and SS phase measurements from a flat surface of an unhardened thermally thick C1018 steel sample. In the SS measurements, three different time constants (1.5 s, 1.0 s and 0.75 s), which correspond to total measurement times of 112 s, 74 s and 58 s, respectively, were used to compare signal quality. It was found that all the curves were similar in shape attesting to the reliability of all the measurements. The difference between lock-in and SS measurement at low frequencies is due to the long time constant (>2 s) used in the lock-in measurements resulting in long-time averaging and slow response. It can be seen that the quality of LIA and SS measurements is comparable. Detailed signal examination reveals that the worst quality is encountered in SS 58-s measurements, which is understandable since the shortest scan-time implies the least photothermal excitation energy input to the system. For total measurement times greater than 58 s (i.e., 74 s and 112 s), the measurement quality is equivalent to that of using a LIA, but with significantly shorter time, which makes the technique more compatible for practical industrial applications.

In conclusion it was demonstrated a quantitative non-destructive technique for evaluating effective case depth in heat treated case-hardened steel products using laser photothermal radiometric (PTR) phase minima. Several types of heat-treated C1018 industrial steel screws (hexagonal, cylindrical and spherical heads) were statistically evaluated and correlation/calibration curves for each type of sample were established using conventional destructive indentation measurements to extract actual hardness case depths. It was found that the PTR thermal-wave interferometric phase minimum determination method is suitable for evaluating case depths $\geqq 300$ μm in this type of steel. The expanded beam measurement scheme generates higher resolution and higher dynamic range than the focused beam scheme. It was shown that PTR thermal-wave interferometric phase-frequency minima coupled with swept-sine waveforms and signal cross-correlation and spectral analysis can be used as a fast on-line inspection method of industrial steel products for quality control of industrial heat treating processes.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method of determining a case depth of a hardened sample comprising a material, said method comprising the steps of:
    a) providing a modulated reference signal;
    b) modulating an intensity of an optical beam according to said modulated reference signal using a modulation means;
    c) measuring an unhardened reference sample comprising said material by scanning a frequency of said modulated reference signal over selected frequencies within a frequency interval, while performing the following steps at each said selected frequency:
        i) irradiating a surface of said reference sample with said optical beam,
        ii) collecting thermal radiation emitted by said reference sample and directing said collected thermal radiation onto a broadband detector;
        iii) determining a reference sample phase difference between a signal obtained from said broadband detector and said modulated reference signal;
    d) measuring said hardened sample by scanning a frequency of said modulated reference signal over said selected frequencies within said frequency interval, while performing the following steps at each said selected frequency:
        iv) irradiating a surface of said hardened sample with said optical beam,
        v) collecting thermal radiation emitted by said hardened sample and directing said collected thermal radiation onto a broadband detector;
        vi) determining a hardened sample phase difference between a signal obtained from said broadband detector and said modulated reference signal;
    e) calculating a normalized phase difference for each said frequency by subtracting said reference sample phase difference from said hardened sample phase difference;
    f) determining a phase-minimum frequency corresponding to a frequency at which said normalized phase difference is minimized; and
    g) relating said phase-minimum frequency to said case depth using a pre-determined calibration curve.

2. The method according to claim 1, wherein said calibration curve is obtained by measuring phase-minimum frequencies of reference samples with known hardness values, and mathematically relating said measured phase-minimum frequencies to said known hardness case depth values.

3. The method according to claim 1 wherein said reference sample comprises one of a flat surface and a curved surface.

4. The method according to claim 1 wherein said frequency interval lies within a range comprising approximately 0.1 Hz and 100 kHz.

5. The method according to claim 1 wherein in steps iii) and vi), a phase of said signal obtained from said broadband detector is determined using one of a lock-in amplifier and a dynamic signal analyzer.

6. The method according to claim 1 wherein in steps ii) and v), said thermal radiation is collected and directed to said detector by an optical fiber bundle.

7. The method according to claim 1 wherein said optical beam is provided by an optical source selected from the list comprising a laser, flashlamp, and light emitting diode.

8. The method according to claim 1 wherein said modulation means is selected from the list comprising optical source current modulation, mechanical chopping, acousto-optic modulation and electro-optic modulation.

9. The method according to claim 1 wherein said material is one of a metal and metal alloy.

10. The method according to claim 1 wherein said material is a ceramic.

11. The method according to claim 1 wherein said optical beam has a diameter within the range of about 1 mm to 22 mm when said optical beam contacts said sample.

12. The method according to claim 1 further comprising passing said collected thermal radiation through a thermal infrared emission filter prior to directing said thermal radiation onto said detector.

13. The method according to claim 1 wherein in step i) and iv), said beam is delivered to said reference sample and said hardened sample by an optical fiber.

14. The method according to claim 13 wherein said optical fiber is provided in an optical fiber bundle, said optical fiber bundle having first, second and third ends, wherein said optical fiber has an input at said first end and an output at second end, and wherein said fiber bundle further comprises one or more additional optical fibers, wherein said one or more additional optical fibers each have an input at said second end and an output at said third end, wherein said thermal radiation is collected by said additional optical fibers at said second end and delivered to said detector at said third end.

15. An apparatus for use in determining a case depth of a hardened sample, said apparatus comprising:
    a) means for providing a modulated reference signal;
    b) an optical source providing an optical beam;
    c) modulation means for modulating an intensity of said optical beam according to said modulated reference signal;
    d) a broadband detector adapted to detect thermal radiation;
    e) an optical fiber bundle having first, second and third ends, said optical fiber bundle comprising a beam delivery optical fiber and one or more collection optical fibers; wherein said beam delivery optical fiber comprises:

an input adapted to receive said optical beam at said first end; and an output adapted to direct said optical beam onto said sample at said second end; and wherein said one or more collection optical fibers each comprise:

an input adapted to collect thermal radiation emitted from said sample at said second end; and an output adapted to direct said collected thermal radiation onto said detector at said third end; and f) processing and output means for determining a phase difference between a phase of a signal obtained from said detector and a phase of said modulated reference signal and one of displaying said phase difference, recording said phase difference, and the combination thereof.

16. The apparatus according to claim 15 further comprising a thermal infrared emission filter located between said third end and said detector.

17. The apparatus according to claim 15 wherein said means for providing a modulated reference signal comprises one of a lock-in amplifier and a dynamic signal analyzer.

18. The apparatus according to claim 15 wherein said modulation means is selected from the list comprising optical source current modulation, a mechanical chopper, an acousto-optic modulator and an electro-optic modulator.

19. The method according to claim 15 wherein said optical beam is provided by an optical source selected from the list comprising a laser, flashlamp, and light emitting diode.

20. The apparatus according to claim 15 wherein said processing and output means comprises a computer.

21. The apparatus according to claim 15 wherein said processing and output means comprises one of a lock-in amplifier and a dynamic signal analyzer.

22. The apparatus according to claim 21 wherein said processing and output means further comprises a computer.

* * * * *

UNITED STATES PATENT AND TRADEMARK OFFICE
Certificate

Patent No. 7,712,955 B2                                                                           Patented: May 11, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Chinhua Wang, Suzhou (CN); Jose A. Garcia, Toronto (CA); and Andreas Mandelis, Scarborough (CA).

Signed and Sealed this Fifth Day of October 2010.

LISA CAPUTO
*Supervisory Patent Examiner*
Art Unit 2855
Technology Center 2800